United States Patent [19]
Ost et al.

[11] 3,975,527
[45] Aug. 17, 1976

[54] AGRICULTURAL PLANT PROTECTION COMPOSITIONS CONTAINING ISOMERS OF TRIFORINE METHOD OF USE

[75] Inventors: Walter Ost, Bingen; Klaus Thomas, Gau-Algesheim; Ekkehard Amadori, Darmstadt-Arheilgen; Rolf Darskus, Gau-Algesheim, all of Germany

[73] Assignee: Celamerck GmbH & Co. KG, Ingelheim am Rhein, Germany

[22] Filed: July 29, 1975

[21] Appl. No.: 600,065

Related U.S. Application Data

[62] Division of Ser. No. 441,010, Feb. 11, 1974, Pat. No. 3,912,738.

[30] Foreign Application Priority Data

| Feb. 10, 1973 | Germany | 2306623 |
| Oct. 15, 1973 | Germany | 2351707 |
| Dec. 21, 1973 | Germany | 2363729 |

[52] U.S. Cl. .................. 424/250; 424/45
[51] Int. Cl.² .......................... A01N 9/22
[58] Field of Search ..................... 424/250

[56] References Cited
UNITED STATES PATENTS
3,696,106  10/1972  Ost et al. .................. 260/268 R

*Primary Examiner*—Frederick E. Waddell
*Attorney, Agent, or Firm*—Hammond & Littell

[57] ABSTRACT

Agricultural plant protection compositions containing as an active ingredient racemic triforine or a mixture thereof with meso-forine, said mixture consisting of at least 60% by weight of racemic triforine and the balance meso-triforine; and a method of using the same for combatting phytopathogenic fungi.

4 Claims, 2 Drawing Figures

ISOMER I

FIG.1  FIG.2

AGRICULTURAL PLANT PROTECTION COMPOSITIONS CONTAINING ISOMERS OF TRIFORINE METHOD OF USE

This is a division of copending application Ser. No. 441,010 filed Feb. 11, 1974, now U.S. Pat. No. 3,912,738.

This invention relates to novel agricultural plant protection compositions, especially fungicidal, compositions, containing as an active ingredient racemic triforine or a mixture consisting of at least 60% by weight of racemic triforine, and the balance meso-triforine, as well as to a method of combatting phytopathogenic fungi therewith.

THE PRIOR ART

U.S. Pat. No. 3,696,106 discloses N,N'-bis-[(1-formamido-2,2,2-trichloro)-ethyl]-piperazine and a method of preparing the same, as well as the broad-spectrum fungicidal properties of this compound against various phytopathogenic fungi.

The Invention

We have discovered that N,N'-bis-[(1-formamido-2,2,2-trichloro)-ethyl]-piperazine (hereinafter sometimes referred to by its generic name "triforine") obtained by the process described in U.S. Pat. No. 3,696,106 actually consists of two components which, by virtue of their different solubilities in certain solvents, can be separated and isolated. With respect to their significant properties for practical employment as fungicides, these two components exhibit considerable differences; and, in addition to differences in solubility, the two components also exhibit differences in other physical-chemical properties, such as their nuclear molecular resonance (NMR) spectra and $R_f$-values.

The triforine molecule comprises two asymmetric carbon atoms with identical substitution, so that in the synthesis of triforine by the prior art process 50% of D,L-triforine (meso-form) and 50% of racemic triforine (25% L,L-triforine and 25% D,D-triforine) are formed.

The above-mentioned components of differing solubility are, on the one hand, the racemate — designated in the following by I — and, on the other hand, the meso-form — designated in the following by II.

Of special importance for practical purposes is that I has a stronger fungitoxic action upon phytopathogenic fungi than either II or the isomeric mixture obtained pursuant to the prior art process.

Surprisingly, mixtures of I and II, wherein the content of I has been enriched to about 60%, also show a considerably stronger fungicidal action than expected. (The percentages here and in the following are percentages by weight, unless otherwise indicated).

Therefore, it is an object of the present invention to provide an industrially feasible process for the production of fungicidally active triforine isomers or isomer mixtures containing at least 60% by weight of I.

In the industrial scale production of triforine from piperazine and tetrachloroethyl-formamide a mixture of isomers I and II is isolated in the approximate weight-ratio of 45 : 55. We have discovered that, when this mixture is treated with a solvent mixture in which the solubility ratio of isomer I to isomer II is at least about 3 : 2, an enrichment in the concentration of I or II is achieved which leads, depending upon the type and quantity of the solvent as well as sometimes also the chosen temperature, to the isolation of the respective pure isomers.

In order to achieve an economic enrichment of isomers, it is of advantage to use solvents which do not only possess a high selectivity with respect to the solubility of I or II therein, but also make it possible to produce solutions of the highest practicable concentration of the isomers to be separated.

The following table shows solubility of the pure isomers I and II in various solvents:

| Solvent | Solubility weight/ unit volume (w/v) at 22°C | | Ratio Solub.I/Solub.II |
|---|---|---|---|
| | I | II | |
| Methanol | 2.8 | 0.6 | 4.7 |
| Cyclohexanone | 3.2 | 1.4 | 2.3 |
| 90% acetone | 5.8 | 1.1 | 5.3 |
| Tetrahydrofuran | 10.4 | 2.0 | 5.2 |
| N-methylpyrrolidone | 22.5 | 28 | 0.8 |
| Dimethylformamide (DMF) | 42 | 15.5 | 2.7 |

Aqueous acetone with a water content of 5 to 20% has proved to be especially suitable for the separation of the isomers. If, for example, aqueous 90% acetone is used, for the extraction of a mixture of about 50% I and II the great difference in solubilities of I and II in this aqueous mixture produces in the liquid phase a strong enrichment of I which is more soluble therein. By means of continuous or repeated extraction, it is possible without difficulties to ultimately obtain a residue consisting exclusively of the more difficultly soluble meso-form II. By evaporation of the extracts, triforine fractions strongly enriched with racemate I are obtained, which by suitable further purification, such as recrystallization from acetonitrile, may be converted into pure racemate I.

A further, especially preferred, embodiment of the isomer enrichment procedure consists of treating technical grade triforine with a quantity of dimethylformamide which is insufficient for a complete dissolution of the compound.

Although the solubility ratio of I and II in DMF of 2.7 is relatively small, the biologically more active form I may surprisingly be separated almost completely from a 1:1-mixture by a single extraction of the isomer mixture with DMF. This method has several decisive advantages in comparison with other enrichment processes:

1. Due to the good solubility of I in DMF, a relatively little solvent is needed for extraction.
2. The yield of extraction of I is almost quantitative, so that there occurs hardly any loss in the desired biologically more active form.
3. Highly concentrated solutions with a content of up to more than 40% w/v of triforine strongly enriched with I are obtained. Without further isolation of the racemate I, these solutions may be used as such for the production of liquid triforine concentrates, since DMF is an especially suitable solvent for such liquid compositions.
4. If it is necessary to isolate the active ingredient dissolved in DMF, the isomer mixture enriched with I may easily be quantitatively precipitated by pouring the DMF-solution into water. Alternatively, the DMF may be distilled off in vacuo.

The separation processes described above lead, in general, to a residue of almost pure form II; however, the isomer I obtained from the solutions always contains about 10 to 30% of the isomer II, as illustrated by the following schematic separation example:

A further enrichment or purification of isomer I is readily feasible by a second purification process, e.g. by a second extraction or by recrystallization, for instance from acetonitrile. It has been noted, however, that it is of advantage for the production of fungicidal compositions, especially of liquid formulations, to use a mixture which still contains a certain proportion of isomer II. Thus, upon dilution of the solution concentrate with water to the desired application concentration, sprays are obtained which are especially stable and do not form any sediment, even after standing for a prolonged time. If pure isomer I is used for production of these solution concentrates, however, it occasionally happens, especially if the hardness of water is very low, that the spray forms considerable quantities of active ingredient sediment after prolonged storage, which may, under certain circumstances cause difficulties when it is used for plant protection.

Therefore, it is a further object of the present invention to provide fungicidal agents or compositions which are characterized by especially high activity against phytopathogenic fungi, and — in case of liquid formulations — yield spray solutions with good stability when diluted with water.

The active ingredients used in accordance with the invention generally contain, besides the isomer II at least about 60% of the isomer I. The content of I amounts preferably to 65 to 97%. Particularly preferred are mixtures of isomers containing 70 to 95%, especially 75 to 90%, of the isomer I.

Pursuant to a preferred embodiment of the invention, therefore, the technical grade mixture of isomers is treated with such quantities of dimethylformamide that extracts are obtained which contain dissolved therein about 25 to 42% of triforine with an isomer-ratio of I : II from about 60:40 to about 90:10. These extracts may be converted by means of suitable additives, such as additional solvents, emulsifiers and optionally de-foamers, directly into liquid formulations (solution concentrates, emulsion concentrates) with the desired content of active ingredient.

A separation of the triforine racemate I into its two optically active components is not possible by conventional methods. The basicity of the triforine racemate, for example, is so low that stable salts with optically active acids cannot be prepared. Also, tests for fractional crystallization of the triforine racemate with optically active solvents are severely limited because of the low solubility of triforine.

Therefore, it is a further object of the present invention to provide a process for isolation of levo-rotatory triforine in optically pure or enriched form. We have discovered that levo-rotatory triforine is characterized by an especially strong fungicidal action.

The following schematic synthesis flow sheet illustrates the preparation of (−), (−)-triforine in accordance with the present invention:

First, piperazine is reacted only at one nitrogen atom with (+), (−)-1,2,2,2-tetrachloroethyl formamide -piperazine form (+),(−)-N-[(1-formamido-2,2,2-trichloro)-ethyl]-piperazne (hereinafter referred to as "mono-triforine"). This compound possesses only one asymmetric center and still exhibits due to the unsubstituted secondary amino group of the piperazine moiety, sufficient basicity for the formation of diastereomeric salts with optically active auxiliary acids. In principle, any desired optically active acid, such as L(+)-lactic acid, D(+)-camphoric acid, D(+)-α-bromocamphor-π-sulfonic acid, (−)-O,O'-dibenzoyl-tartaric acid, (+)-mandelic acid, (−)-mandelic acid, L(−)-malic acid or L-(−)-5-pyrrolidinone-2-carboxylic acid may be used for production of diastereomeric salts of mono-triforine. However, especially suitable as a salt-forming auxiliary acid is L(+)-tartaric acid, because we have found that the two diastereomeric hydrogen tartrates of mono-triforine may be separated, based on their different tendencies toward solvate formation and strongly differing solubilities of the solvates, with excellent yields and without great purification expenditures.

If the mixture of diastereomeric hydrogen tartrates is dissolved in water, the (−)-mono-triforine-hydrogen tartrate crystallizes out as pentahydrate with a yield of more than 90% and with an optical purity of 98%. By recrystallization from water, the optical purity can be increased to above 99.5%.

The aqueous filtrate contains (+)-mono-triforinehydrogen tartrate, which is very freely soluble in water. After distilling off the water and treating the residue with 96% ethanol, the (+)-mono-triforine-hydrogen tartrate is obtained as crystalline ethanol solvate with over 80% yield and an optical purity of over 99%.

The separated diastereomeric mono-triforine-hydrogen tartrates may be converted by treatment with alkali, in aqueous solution, into the optically pure bases with specific rotations of −63.0° and +62.6°, respectively. Here, too, further purification is not required.

In the next synthesis step, optically pure (−)-mono-triforine is reacted again with (+), (−)-1,2,2,2-tetrachloroethyl-formamide. In this manner a mixture consisting of 50% meso-triforine and 50% (−), (−)-triforine is obtained. Correspondingly, from (+)-mono-triforine a mixture of 50% meso-triforine and 50% (+), (+)-triforine is formed.

Separation of these mixtures into the corresponding isomers is effected by fractional crystallization or fractional extraction. In this manner the 2- to 6-fold greater solubility of levo-rotatory and dextro-rotatory triforine, respectively, compared to meso-triforine is exploited. Especially suitable as solvents are methanol, acetone with up to 20% water added, tetrahydrofuran, acetonitrile or dimethylformamide. An enrichment in (−),(−)-triforine is possible, for example, by extraction of the mixture of levo-rotatory triforine and meso-triforine with aqueous 90% acetone, boiling methanol, tetrahydrofuran or dimethylformamide (DMF). Here, the extraction with a quantity of DMF insufficient for a complete dissolution of the mixture of isomers represents an especially preferred embodiment of the enrichment in (−),(−)-triforine, because DMF possesses a good dissolving capability for levo-rotatory triforine and, moreover, these solutions may be used directly for production of highly effective compositions for plant protection. If it is desired to isolate enriched levo-rotatory triforine as a solid material, the substance may be precipitated by pouring the DMF solution into water, or by distilling off the solvent in vacuo.

In order to isolate the optically pure isomers, it is advantageous to first separate the major amount of the meso-form by selective extraction, and then recrystallize the enriched optically active product containing about 65 to 90% of levo-rotator triforine. Especially suitable as solvents for recrystallization are methanol and acetonitrile.

For isolation of small quantities of the pure isomers, mechanical separation methods may be applied as well, because under certain conditions the meso-form and optically active triforine separate out in different, well-defined forms of crystals. Upon slow crystallization of mixture of the meso-form and (−),(−)-triforine from acetonitrile, meso-triforine crystallizes out, for example, in the form of clear, colorless prisms, while levo-rotatory triforine separates out in the form of bundles of colorless needles.

It is of special significance for the practice of plant protection, that the three triforine isomers exhibit very different fungitoxic actions upon various phytopathogenic fungi. Biological examination of the three isomers showed a decrease in fungitoxic action in the sequence (−),(−)-triforine >> meso-triforine > (+),(+)-triforine.

Consequently, by far the biologically most active form is levo-rotatory triforine. Thus, it has become possible by virtue of the process of preparation of or enrichment in (−),(−)-triforine according to the instant invention to make available for plant protection an active ingredient which considerably surpasses the triforine isomer mixture in its effectiveness against phytopathogenic fungi.

For economic reasons it is of advantage not to use levo-rotatory triforine in its optically pure form for production of plant-protecting compositions, but as a mixture enriched to 45 – 95%.

While normal technical grade triforine contains only about 25% of the levo-rotatory isomer, the procedure pursuant to the present invention described in Example 3d below already yields, without further enrichment, a product containing about 50% (−),(−)-triforine. By means of a subsequent selective extraction procedure pursuant to Example 4 below, a triforine solution is obtained wherein the dissolved triforine contains about 80% of the (−),(−)-form. Thus, the expensive fractional crystallization procedure is required only if optically completely pure (−),(−)-triforine is to be produced, which is not essential for plant-protecting purposes.

Liquid formulations with levo-rotatory triforine-enriched active ingredient content are preferably produced by diluting a high-percentage active ingredient solution in a suitable solvent, preferably in DMF, obtained pursuant to Example 4 to the desired active ingredient concentration with additives, such as emulsifiers, optionally further solvent and de-foamers.

Solid formulations with pure or enriched (−),(−)-triforine content, such as suspension powders, granulates and dusting powders, are prepared in conventional manner by adding the conventional excipients and carriers.

The isomer I which is obtained upon separation of isomers I and II or during the production of levo-rotatory triforine is, as already explained, less desirable for fungus control.

The present invention also solves the further problem to convert meso-triforine (II) by racemization into the biologically more active racemic form (I).

In solid form, I and II are stable under normal conditions; after several years' storage at room temperature no isomerization could be noted.

In solutions, too, there is no isomerization at room temperature and below.

We have now found that II can be isomerized into I in solution at elevated temperature. Since the equilibrium ratio between I and II is about 1:1, the conversion in one step may lead to a maximal yield of 50%. By repetition of the isomerization process with the meso-form, which is always re-obtained after separation of the racemate, a practically complete conversion may gradually be effected.

The isomerization may advantageously be carried out as a continuous process by removing the racemate continuously from the reaction solution. Due to the considerably higher solubility of the racemate in comparison to the mesoform, this continuous process is relatively easily performable on a technical scale in most of the solvents suitable for isomerization.

Especially suitable as solvents for isomerization are dimethylformamide, N-methylpyrrolidone, dimethylacetamide, hexamethyl phosphoric acid triamide, caprolactam, phenol or mixtures of these solvents. The advantage of the above solvents is their good dissolving power for the triforine isomers. However, other solvents, such as dimethylsulfoxide, tetrahydrofuran, cyclohexanone, butyrolactone, acetone, acetonitrile or methanol may be used, either by themselves or in an admixture with other solvents. The addition of water (for example, 3–20 volume-% in the case of the ketones) may also be of advantage.

When choosing the reaction temperature, it has to be considered that while the isomerization rate greatly increases with increasing temperature in most of the solvents, elevated temperatures may also cause losses of active ingredient due to decomposition. The most favorable temperature range for isomerization is about 40° to 100°C, and the preferred range is from 60° to 100°C.

The isomerized triforine solutions may be purified by pouring them into water. Possibly formed degradation products are easily soluble in water, while the active ingredient, due to its low water-solubility, precipitates quantitatively from water. By washing the crystallizate with water and drying it, the isomer mixture is obtained which may either be used directly for the production of plant-protection compositions or processed further pursuant to the process described above.

If isomerization conditions are chosen under which there is practically no degradation of the active triforine ingredient, the reaction solutions may be processed into plant-protecting compositions, especially liquid formulations, witout isolating the active triforine ingredient.

The following examples further illustrate the present invention and will enable others skilled in the art to understand it more completely. It should be understood, however, that the invention is not limited solely to the particular examples given below.

EXAMPLE 1

200 gm of finely milled triforine (isomer ratio I: II = 48;52) were stirred with 1000 ml of aqueous 90% acetone for 1 hour at 22°C. The undissolved triforine residue was filtered off and dried, and the acetone extract was evaporated in vacuo, whereby 140 gm of filter residue and 60 gm of evaporation residue were obtained. The filter residue was treated again with 5 times its amount (700 ml) of aqueous 90% acetone like before, and the separation process was repeated twice with each of the residues:

|  | Amount used of | | filter residue | evaporation residue |
|---|---|---|---|---|
|  | triforine | acetone | | |
| 1st extraction | 200 gm | 1000 ml | 140 gm | 60 gm |
| 2nd extraction | 140 gm | 700 ml | 95 gm | 45 gm |
| 3rd extraction | 95 gm | 475 ml | 75 gm | 20 gm |
| 4th extraction | 75 gm | 375 ml | 67 gm | 8 gm |

For further purification, the evaporation residues of the first and the second extractions (total 105 gm) were recrystallized from 1700 ml of acetonitrile. 70 gm of almost pure isomer I were obtained, which were recrystallized once more from 1200 ml of acetonitrile. In this way, 48 gm of analytically pure I were obtained in the form of well-defined, glass-clear colorless crystals.

| Decomp. point | 179°C | C | calc. 27.61% | found 27.98% |
|---|---|---|---|---|
| $R_f$-value | 0.51 | H | calc. 3.24% | found 3.35% |
| (silicagel: chloroform/methyl-glycol 9:1) | | Cl | calc. 48.91% | found 48.98% |
| | | N | calc. 12.88% | found 12.69% |

For isolation of the pure isomer II, the 67 gm of filter residue of the fourth extraction were boiled twice with 350 ml each of acetonitrile. 63 gm of analytically pure II were obtained. A 0.5 gm-sample was recrystallized from 75 ml of acetonitrile. The obtained 0.35 gm of II did not differ in elemental analysis, decomposition point, thinlayer chromatogram, NMR and IR-spectrum from the main quantity extracted by boiling.

| Decomp. point | 181°C | C | calc. 27.61% | found 27.79% |
|---|---|---|---|---|
| $R_f$-value | 0.57 | H | calc. 3.24% | found 3.50% |
| (silicagel: chloroform/methyl-glycol 9:1) | | Cl | calc. 48.91% | found 48.70% |
| | | N | calc. 12.88% | found 12.64% |

Figure 1:
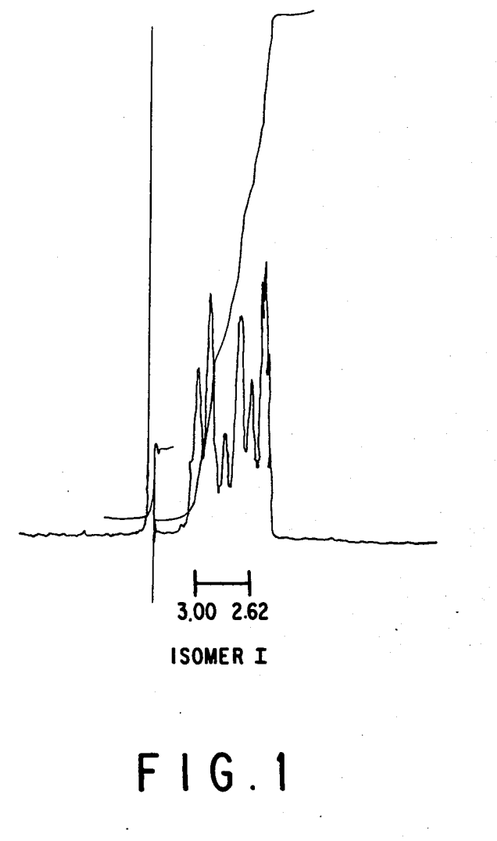
FIG. 1 is the NMR-spectrum for I and FIG. 2 is the NMR-spectrum for II.
Figure 2:
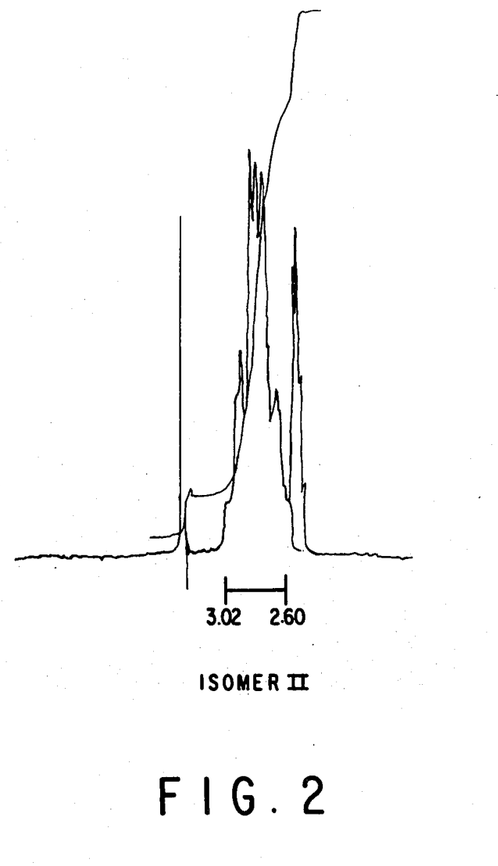

NMR-spectra (100 megacycle-spectrum, solvent DMSO-d$_6$; temperature 28°C).

In the case of I, the methylene protons of the piperazine ring produced a symmetrical multiplet of 2.62 to 3.00 ppM ($\delta$), while in the case of II, a value of 2.60 to 3.02 ppM ($\delta$) was found.

The corresponding sections of the NMR-spectra are shown in the attached drawings, where.

EXAMPLE 2

1000 gm of technical grade, finely milled triforine (content of pure triforine: 99%, ration of isomers I : II = 47:53) were suspended in 1000 ml of dimethylformamide (DMF). The suspension was stirred for 1 hour at 22°C, and was then vacuum-filtered. The filter cake was washed twice with 50 ml each of DMF. A total of 1220 ml of filtrate with a density of 1.11 were obtained.

Quantitative analysis showed that the obtained DMF solution contained a total of 522 gm of active triforine substance (= 42.8% w/v), consisting of 440 gm I and 82 gm II (i.e. the ratio I : II = 84 : 16). Thus, an enrichment of isomer I from 47% to 84% had taken place with a I-yield of more than 93%.

In order to isolate the I-enriched active triforine substance, the DMF-solution was poured into 10 times its volume of water. The precipitated active triforine substance was vacuum-filtered off, washed with water until free from DMF and dried at 80°C. A yield of 99% (based on the total quantity dissolved in DMF) of active triforine substance with the same ratio of I : II which was present in the DMF solution (here I : II = 84 : 16), was obtained.

The extraction residue was treated with 3 liters of water, vacuum-filtered, washed with water until free from DMF and dried at 80°C. 469 gm of residue with a ratio of isomers of I : II = 6 : 94 were obtained.

EXAMPLE 3 a.

(+),(−)-N-[(1-Formamido-2,2,2-trichloro)-ethyl]piperazine

A solution of 220 gm (1.04 mol) of (+),(−)-1,2,2,2-tetrachloroethyl-formamide in 400 ml of acetone and a solution of 140 gm (1.03 mol) of sodium acetate trihydrate in 200 ml of water were simultaneously added dropwise to a solution of 86 gm (1 mol) of piperazine in a mixture of 80 ml of 12.5 N hydrochloric acid (1 mol) of 800 ml of water, while stirring. The initially clear solution became gradually turbid, and a colorless, viscous precipitate formed.

After stirring for 30 minutes at 3°–5°C, a solution of 170 ml of 6N sodium hydroxide (1.02 mol) was added at that temperature. The acetone was distilled off in vacuo at room temperature, and the precipitated crystals of N,N'-bis-[(1-formamido-2,2,2-trichloro)-ethyl]-piperazine were collected by vacuum filtration (36.5 gm). The aqueous filtrate was saturated with about 500 gm of sodium chloride, whereby the hydrochloride of the compound named in the heading separated out in crystalline form. The crystals were collected by vacuum filtration and dissolved in 1000 ml of water, a small amount of insoluble matter was filtered off, and while cooling, the filtrate was admixed with 170 ml of 6N sodium hydroxide (1.02 mol).

The colorless product which crystallized out was collected by vacuum filtration, washed with water until free from sodium chloride and dried at no more than 50°C. 179 gm (68.8% of theory) of pure (+),(−)-N-(1-formamido-2,2,2-trichloroethyl)-piperazine, m.p. 133°–134°C, were obtained.

No further purification effect was achieved by recrystallization from ethylacetate.

b.
(−)-N-[(1-formamido-2,2,2-trichloro)-ethyl]-piperazine L(+)-hydrogen tartrate pentahydrate 156 gm (0.6 mol) of (+),(−)-N-[(1-formamido-2,2,2-trichloro)-ethyl]-piperazine and 93 gm (0.62 mol) of L(+)-tartaric acid were dissolved at 30°–40°C in 800 ml of deionized water, and the solution was allowed to stand for about 24 hours at +5°C. Thereafter, the supernatant liquid was carefully decanted from the large, clear crystals, and the crystallizate was washed twice with a little ice water. The residue was air-dried at room temperature. 138.9 gm (92.5% of theory) of (−)-N-(1formamido-2,2,2-trichloroethyl)-piperazine L(+)-hydrogen tartrate pentahydrate were obtained. $[\alpha]_D^{23}$ : −21.7° (water; c = 6) (optical purity 98.1%).

Upon recrystallizing the product once from 6 parts of water at no more than 50°C the compound was obtained with an optical purity of 100%; $[\alpha]_D^{23}$ : −24.8° (water; c = 6).

$C_7H_{12}Cl_3N_3O \cdot C_4H_6O_6 \cdot 5\ H_2O$
| Calculated: | 27.4% C | Found: | 27.5% C |
|---|---|---|---|
| | 5.6% H | | 5.5% H |
| | 8.4% N | | 8.3% N |
| | 21.3% Cl | | 21.2% Cl | c.
(−)-N-[(1-formamido-2,2,2-trichloro)-ethyl]-piperazine 250 gm (0.5 mol) of (−)-N-[(1-formamido-2,2,2-trichloro)-ethyl]-piperazine L(+)-hydrogentartrate pentahydrate were suspended in 1500 ml of water. While cooling and stirring the suspension, 490 ml of 2N sodium hydroxide (0.98 mol) were added dropwise at about 5°C internal temperature. Subsequently, 700 gm of sodium chloride were added, the mixture was stirred for 1 hour at 5° to 10°C, the fine, crystalline, colorless precipitate formed thereby was collected by vacuum filtration and washed twice with 150 ml each of ice water. The product was dried at room temperature. Yield: 114.5 gm (88.2% of theory); m.p. 140°–142°C $[\alpha]_D^{23}$ : −63.0° (ethanol; c = 6) (optical purity 99.5%).

d. Mixture of (+),
(−)-N,N'-bis-[(1-formamido-2,2,2-trichloro)-ethyl]-piperazine (meso-triforine) and
(−),(−)-N,N'-bis-[(1-formamido-2,2,2-trichloro)-ethyl]-piperazine (levo-rotary triforine)

A solution of 63.3 gm (0.3 mol) of (+),(−)-1,2,2,2-tetrachloroethyl-formamide in 300 ml of ethylacetate (analytically pure) was added dropwise at +4°C over a period of about 20 minutes to a suspension of 78.2 gm (0.03 mol) of (−)-N-[(1-formamido-2,2,2-trichloro)-ethyl]-piperazine in a mixture of 30.3 gm (0.3 mol) of triethylamine and 300 ml of ethylacetate (analytically pure), while stirring. The resulting mixture was stirred for 1 hour more at no more than 5°C, and the colorless crystal mixture was collected by vacuum filtration and washed with 100 ml of ethylacetate.

The dried, pulverized residue was treated with 600 ml of water, vacuum-filtered and washed with water until free of chloride. The resulting mixture of meso-triforine and levo-rotatory triforine was dried in vacuo at no more than 60°C. 115 gm of triforine (= A) were obtained; m.p. 175°–176°C (decomp.); $[\alpha]_D^{23}$ : −40.4° (DMF; c = 6) (ratio of meso-triforine : levo-rotatory triforine = 51.5 : 48.5).

The combined ethyl acetate filtrates were evaporated in vacuo below 40°C, and the semi-solid residue was shaken with a mixture of 200 ml of water and 200 ml of methylene chloride. The methylene chloride phase was separated and allowed to stand for about 20 hours at 0° – 10°C. The triforine precipitate formed thereby was collected by vacuum filtration, washed with water and methylenechloride, and dried below 60°C.

Another 6.8 gm of triforine, m.p. 173°–175°C (decomp.) (= B), were obtained). $[\alpha]_D^{23}$ : −73.6° (DMF; c = 6) (ratio of meso-triforine : levo-rotatory triforine = 12:88). Total yield of triforine: 121.8 gm = 93.4% of theory.

e. Separation of
(+),(−)-N,N'-bis-[(1-formamido-2,2,2-trichloro)-ethyl]-piperazine and
(−),(−)-N,N'-bis-[(1-formamido-2,2,2-trichloro)-ethyl]-piperazine I. Production of Seed Crystals 6 gm of pulverized B (ratio of triforine isomers = 12 : 88) were dissolved in 135 ml of warm acetonitrile, and the solution was allowed to stand at room temperature without agitation for 90 hours. Thereafter, the mother liquor was carefully decanted from the crystals which had formed, and the crystals were washed twice with acetonitrile, yielding bundles of colorless needles, m.p. 173°–175°C (decomp.); $[\alpha]_D^{23}$ : −82.2° (DMF; c = 6); ratio of levo-rotatory triforine : meso-triforine = 98.5 : 1.5). Upon one more recrystallization from acetonitrile, levo-rotatory triforine was obtained practically without any meso-form impurity. $[\alpha]_D^{23}$ : −83.2° (DMF; c = 6; optical purity > 99%).

II. Separation of major amount of isomer mixture 114 gm of the mixture of meso-triforine and levorotatory triforine obtained in Example 3d (= A; ratio of isomers = 51.5 : 48.5) were finely pulverized and refluxed for 5 minutes, while stirring, with 580 ml of analytically pure methanol. The resulting suspension was vacuum-filtered while still hot on a preheated suction filter (filter cake = II A). The filtrate was diluted to 580 ml of methanol (analytically pure), heated again to the boiling point, filtered while hot to remove a small amount of undissolved material, and evaporated in vacuo.

59 gm of a crystalline residue (= II B) were obtained. $[\alpha]_D^{23}$ : −63.8° DMF; c = 6) (ratio of levo-rotatory triforine : meso-triforine = 76.5 : 23.5).

58 gm of II B were dissolved in 700 ml of boiling analytically pure methanol. The warm solution was seeded with meso-triforine (preparation see below) and allowed to stand for 24 hours at room temperature. The supernatant methanol solution was decanted from the separated crystals which consisted mostly of meso-triforine, and the solvent was distilled off in vacuo.

35.9 gm of already highly enriched (−),(−)-triforine remained (= II C). $[\alpha]_D^{23}$ : −74.0° (DMF; c = 6) (ratio of levo-rotatory triforine : meso-triforine 89 : 11).

30 gm of pulverized II C were dissolved in 600 ml of boiling acetonitrile, the solution was seeded with seed crystals of pure (−),(−)-triforine obtained in Example 3e)I, and the mixture was allowed to stand for 72 hours at room temperature. The crystallizate was collected by vacuum filtration, washed with acetonitrile and purified twice more in the same way by recrystallization from acetonitrile. 8.6 gm of pure (−),(−)-triforine of m.p. 176°–177°C (decomp.) were obtained. $[\alpha]_D^{23}$ : −83.0°C (DMF; c = 6) (optical purity >99%). $R_f$-value 0.50 (chloroform/methylgylcol 9 : 1 on silicagel).

Analysis: $C_{10}H_{14}Cl_6N_4O_2$
Calculated: 27.60% C
3.24% H
12.88% N
48.91% Cl Found: 27.72% C
3.50% H
12.75% N
49.15% Cl Filter cake II A of the methanol extraction was extracted again with 300 ml of boiling methanol and subsequently with 500 ml of boiling acetonitrile. The remaining product was optically inactive and practically pure meso-triforine. The product was recrystallized from 150 parts of boiling acetonitrile, whereupon it had a melting point of 180°C (decomp.); $[\alpha]_D^{23}$ : 0° (DMF; c = 6). $R_f$-value 0.57 (chloroform/methylglycol 9 : 1 silicagel)

Analysis: $C_{10}H_{14}Cl_6N_4O_2$
Calculated: 27.60% C
3.24% H
12.88% N
48.91% Cl Found: 27.77% C
3.38% H
12.61% N
48.75% Cl Analogously, dextro-rotatory triforine was obtained from (+)-N-(1-formamido-2,2,2-trichloroethyl)-piperazine and D,L-1,2,2,2-tetrachloroethylformamide. First, the mixture of isomers with a specific rotation of +38.4° (in DMF) was obtained, and from this isomer mixture pure (+),(+)-N, N′-bis-[(1-formamido-2,2,2-trichloro)-ethyl]-piperazine, m.p. 174°–175°C (decomp.), $[\alpha]_D^{23}$ : +83.7° (DMF, c = 6), optical purity > 99.5%, $R_f$-value 0.50 (chloroform/methylglycol 9:1 on silicagel), was isolated by fractional crystallization.

EXAMPLE 4

Enrichment of (−),(−)-N,N′-bis-(1-formamido-2,2,2-trichloro)-ethyl]-piperazine 130 gm (0.3 mol) of a finely pulverized mixture of (−),(−)-triforine and meso-triforine ($[\alpha]_D^{23}$ = −40.2°; ratio of levo-rotatory triforine : meso-triforine = 48 : 52), prepared according to Example 3d, were stirred with 150 ml of dimethylformamide for 2 hours at 40°C and subsequently for 2 hours at +20°C. Thereafter, the resulting suspension was vacuum-filtered, and the filter cake washed twice with 10 ml each of DMF. The residue was suspended in 200 ml of water, the suspension was vacuum-filtered, and the filter cake was washed with water and dried below 60°C. 53.1 gm of a substance having a m.p. of 176°–178°C (decomp.) were obtained. $[\alpha]_D^{23}$ : −4.7° (DMF, c = 6) (ratio of levo-rotatory triforine : meso-triforine = 5.5 : 94.5).

The combined DMF-filtrates amounting to a total of 188 ml contained 76 gm (= 40.5% w/v) of triforine, made up of 78.5% levo-rotatory triforine and 21.5% meso-triforine. Yield of extraction of (−),(−)-triforine 96% of theory. (The ratio of isomers was determined densitometrically). The (−),(−)-triforine-enriched DMF solution can be processed directly into a liquid plant-protecting composition (see Example 5).

In order to isolate the levo-rotatory triforine-enriched mixture as a solid substance, 94 ml of the DMF solution were stirred into 1500 ml of cold water. After stirring for 15 minutes, the precipitated substance was collected by vacuum-filtration, washed with water and dried below 60°C. 37.2 gm of triforine, m.p. 174°–176°C (decomp.), were obtained; $[\alpha]_D^{23}$ : −65.2° (DMF; c = 6), ratio of levo-rotatory triforine - meso-triforin = 78 : 22.

EXAMPLE 5

Solution Concentrate 37.1 ml of the 40.5% triforine solution in DMF enriched with levo-rotatory triforine obtained in Example 4 were admixed with 10 gm of the isopropylamine salt of the dodecylbenzene sulfonic acid and 3 gm of isohexadecanol, and the mixture was diluted with N-methyl-pyrrolidine to 100 ml. A liquid concentrate was obtained with a 15% w/v content of triforine (ratio of (−),(−)-triforine : meso-triforine = 78.5 : 21.5). The ratio of isomers remained unchanged after 4 months of shelf storage at 22°–28°C. By dilution with water, the liquid concentrate may be adjusted to the desired concentration for use as a fungicidal plant spray.

EXAMPLE 6

Aerosol Spray

Composition:
(-),(-)-triforine($[\alpha]^{23}_D$ : −82.5°;
optical purity 98.5%) 0.05%
Sesame oil 0.10%
Dimethylformamide 10.00%
Frigens 89.85%

EXAMPLE 7

Suspension Powder

Composition:
(-),(-)-triforine ($[\alpha]^{23}_D$ : −74.0°C;
optical purity 89%) 30%
Kaolin 50%
Colloidal silicic acid 10%
Lignin sulfonate 9%
Sodium tetrapropylene benzenesulfonate 1%

Instead of the (−),(−)-triforine with an optical purity of 89%, triforine with a higher or lower content of the pure levo-rotatory form, especially the pure optical isomer, may also be used.

By milling the mixed components, a suspension powder is obtained, which may be diluted with water to the desired concentration for use as a fungicidal plant spray.

EXAMPLE 8

20 gm of meso-triforine were heated to 60°C in a mixture of 43 gm of dimethylformamide and 43 gm of N-methylpyrrolidone (total volume of the solution at room temperature: 100 ml). The ratio of isomers after various periods of time, as well as the yield of racemates is shown in the following table:

| Isomerization time ($\alpha$°C) | Ratio of isomers racemate: meso-form | Total active ingredient content of solution | Yield of racemate |
|---|---|---|---|
| 0 days | 0 : 100 | 20.0 gm | — |
| 9 days | 32 : 68 | 19.0 gm | 6.1 gm |
| 15 days | 38 : 62 | 18.2 gm | 6.9 gm |
| 30 days | 49 : 51 | 16.9 gm | 8.3 gm |

EXAMPLE 9

A solution produced as described in Example 8 was kept at 70° instead of 60°C. The yield of racemate after various time periods is shown in the following table:

| Isomerization time (70°C) | Ratio of isomers racemate: meso-form | Total active ingredient content of solution | Yield of racemate |
|---|---|---|---|
| 0 days | 0 : 100 | 20.0 gm | — |
| 2 days | 33 : 67 | 17.6 gm | 5.8 gm |
| 5 days | 48 : 52 | 15.6 gm | 7.5 gm |

EXAMPLE 10

A solution of 50 gm of meso-triforine in 150 ml of dimethylformamide was heated to 90°C for 4 hours, and the resulting brownish solution was stirred into 1500 ml of water after cooling. The precipitate formed thereby was collected by vacuum-filtration, washed with water and dried at 60°C. Yield: 47 gm (94% of the starting quantity). Ratio of racemate : meso-form = 41 : 59; i.e. a yield of racemate of 19.3 gm.

EXAMPLE 11

A mixture of 50 gm of meso-triforine and 100 ml of N-methylpyrrolidone was heated to 95°C for 3½ hours. After cooling, the resulting solution was diluted with 1000 ml of water, and the crystallizate was collected by vacuum filtration, washed with water and dried at 60°C. 46 gm of a mixture of isomers was obtained with a ratio of racemate: meso-form = 42.5 : 57.5, i.e. a yield of racemate of 19.5 gm.

EXAMPLE 12

A mixture of 46 gm of meso-triforine, 400 ml of cyclohexanone and 20 ml of water was heated to 95°C for 8 hours, whereby a milky-turbid solution was formed. The cyclohexanone was distilled off as far as possible, and the residue was washed with water, vacuum-filtered and extracted with 50 ml of dimethylformamide at room temperature. The extracted filtrate was diluted with 500 ml of water, and the precipitate formed thereby was collected by vacuum filtration, washed with water and dried at 60°C.

19 gm of triforine were obtained with a ratio of racemate : meso-form = 79 : 21, i.e. the yield of racemate amounted to 15.0 gm.

For agricultural plant protection purposes, the triforine isomers according to the present invention are incorporated as active ingredients into conventional agricultural plant protection compositions, that is, compositions consisting essentially of an inert solid or liquid carrier and an effective plant-protecting, especially fungicidal amount of the active ingredient, such as dusting powders, granulates, wettable suspension powders, emulsion concentrates, sprays and the like. The effective active ingredient concentration range in liquid forms of such compositions is 0.001 to 0.1% by weight, preferably 0.004 to 0.05% by weight, based on the total weight; in ultra-low-volume compositions and dusting powders the active ingredient concentration may also be higher (up to about 85% by weight).

The following examples illustrate a few agricultural plant protection compositions comprising an isomeric triforine of the present invention as an active ingredient and represent the best modes contemplated of putting the invention into practical use. The percentages are percentages by weight unless otherwise specified.

EXAMPLE 13

Dusting Powder

The composition is compounded from the following ingredients:

| | |
|---|---|
| Isomeric triforine of the instant invention | 1% |
| Talcum | 98% |
| Methyl cellulose | 1% |

The ingredients are admixed, and the mixture is milled into a homogeneous powder.

EXAMPLE 14

Wettable Suspension Powder

The composition is compounded from the following ingredients:

| | |
|---|---|
| Isomeric triforine of the instant invention | 25% |
| Kaolin | 55% |
| Colloidal silicic acid | 10% |
| Lignin sulfonte (dispersing agent) | 9% |
| Sodium tetrapropylenebenzene sulfonate (wetting agent) | 1% |

The ingredients are admixed, the mixture is milled into a homogeneous powder, and prior to use the powder is suspended in a sufficient amount of water to make a sprayable aqueous suspension with an active ingredient content of 0.001 to 0.5%.

EXAMPLE 15

Aerosol Spray

The composition is compounded from the following ingredients:

| | |
|---|---|
| Isomeric triforine of the instant invention | 0.05% |
| Sesame oil | 0.10% |
| N-methylpyrrolidone | 10.00% |
| Frigen propellants | 89.85% |

The ingredients are admixed and filled into aerosol spray cans in the conventional manner.

EXAMPLE 16

Solution concentrate 58.5 ml of the 42.8% triforine solution in DMF obtained in Example 2 are admixed with 25 gm of the isopropylamine salt of dodecylbenzene sulfonic acid. By addition of DMF (about 27 ml) the mixture is diluted to 100 ml. In this manner a solution concentrate with a content of 25% w/v of isomeric triforine (ratio of I : II = 84 : 16) is obtained, which can be diluted with water to the desired concentration for use.

EXAMPLE 17

Solution Concentrate 35.1 ml of the 42.8% triforine solution in DMF obtained in Example 2 are admixed with 15 gm of the ethanolamine salt of dodecyl benzenesulfonic acid, 5 gm of 2-ethyl-3-octyl-ethanol and 12 ml of xylene. The mixture is diluted with N-methylpyrrolidone (about 36 ml) to 100 ml. A solution concentrate with a content of 15% w/v of isomeric triforine (ratio of I : II = 84 : 16) is obtained, which can be diluted with water to the required concentration for use.

EXAMPLE 18

Solution Concentrate 10 gm of the pure triforine isomer I obtained in Example 1 are dissolved in 40 ml of DMF. 15 gm of the isopropylamine salt of dodecyl benzene sulfonic acid are added to the solution and the mixture is thoroughly mixed and diluted with N-methylpyrrolidone to 100 ml. A solution concentrate is obtained with a content of 10% w/v of the triforine isomer I. By diluting the concentrate with water to the desired active ingredient concentration, an effective spray for use in plant protection is obtained.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. An agricultural plant protection composition consisting essentially of an inert carrier and an effective fungicidal amount of racemic triforine or a mixture thereof with meso-triforine, said mixture consisting of at least 60% by weight of racemic triforine and the balance meso-triforine.
2. A composition of claim 1, where said mixture consists of 70 to 95% by weight of racemic triforine and the balance meso-triforine.
3. The method of combatting phytopathogenic fungi, which comprises contacting said fungi with an effective fungitoxic amount of racemic triforine or a mixture thereof with meso-triforine, said mixture consisting of at least 60% by weight of racemic triforine and the balance meso-triforine.
4. The method of claim 3, where said mixture consists of 70 to 95% by weight of racemic triforine and the balance meso-triforine.

* * * * *

UNITED STATES PATENT OFFICE
CERTIFICATE OF CORRECTION

Patent No. 3,975,527　　　　　　　Dated August 17, 1976

Inventor(s) Walter Ost et al.

It is certified that error appears in the above-identified patent and that said Letters Patent are hereby corrected as shown below:

Title of invention should read -- AGRICULTURAL PLANT PROTECTION COMPOSITIONS CONTAINING ISOMERS OF TRIFORINE AND METHOD OF USE --.

Column 1, line 4, "TRIFORINE METHOD OF USE" should read -- TRIFORINE AND METHOD OF USE --.

Column 6, lines 42 and 43, "formamide -pi-perazine" should read -- formamide to --.

Column 6, line 44, "piperazne" should read -- piperazine --.

Column 7, line 54, before "mixture" insert -- a --.

Column 7, line 66, "for" should read -- far --.

Column 8, line 35, "I" should read -- II --.

Signed and Sealed this

Eighteenth Day of October 1977

[SEAL]

Attest:

RUTH C. MASON
Attesting Officer

LUTRELLE F. PARKER
Acting Commissioner of Patents and Trademarks